United States Patent
Kelly, Jr. et al.

[11] Patent Number: 5,961,465
[45] Date of Patent: Oct. 5, 1999

[54] ULTRASOUND SIGNAL PROCESSING ELECTRONICS WITH ACTIVE COOLING

[75] Inventors: Walter Patrick Kelly, Jr., Dracut; Benjamin M. Herrick, Boxborough, both of Mass.

[73] Assignee: Hewlett-Packard Company, Palo Alto, Calif.

[21] Appl. No.: 09/021,550

[22] Filed: Feb. 10, 1998

[51] Int. Cl.⁶ ........................................................ A61B 8/00
[52] U.S. Cl. ................................................................ 600/459
[58] Field of Search .................................. 600/437, 443, 600/447, 459–471

[56] References Cited

U.S. PATENT DOCUMENTS

| | | |
|---|---|---|
| 4,375,818 | 3/1983 | Suwaki et al. |
| 4,748,985 | 6/1988 | Nagasaki . |
| 4,815,470 | 3/1989 | Curtis et al. |
| 4,844,080 | 7/1989 | Frass et al. |
| 5,020,539 | 6/1991 | Yokoi et al. |
| 5,158,087 | 10/1992 | Gatzke . |
| 5,163,433 | 11/1992 | Kagawa et al. |
| 5,181,514 | 1/1993 | Solomon et al. |
| 5,213,103 | 5/1993 | Martin et al. ............................ 600/443 |
| 5,226,422 | 7/1993 | McKeighen et al. |
| 5,243,989 | 9/1993 | Saiga et al. |
| 5,320,104 | 6/1994 | Fearnside et al. |
| 5,353,798 | 10/1994 | Sieben . |
| 5,380,274 | 1/1995 | Nita . |
| 5,555,887 | 9/1996 | Fraser et al. ............................ 600/472 |
| 5,560,362 | 10/1996 | Sliva, Jr. et al. |
| 5,590,658 | 1/1997 | Chiang et al. |
| 5,690,114 | 11/1997 | Chiang et al. ............................ 600/447 |

FOREIGN PATENT DOCUMENTS

WO94/14379  7/1994  WIPO .

Primary Examiner—Francis J. Jaworski

[57] ABSTRACT

An ultrasound transducer structure in accord with the invention includes: an ultrasound transducer operable to generate and receive ultrasonic energy, a communication cable, integrated circuits for processing signals received from said ultrasound transducer and flexible circuits for connecting the communication cable to the integrated circuit, and for further connecting the integrated circuits to the ultrasound transducer. A housing contains the ultrasound transducer, the integrated circuits and the flexible circuits. A heat transfer structure is positioned within the housing and is in contact with the integrated circuit. A heat conductor resides in contact with the heat transfer structure and conducts heat generated by the integrated circuits to a heat sink.

8 Claims, 7 Drawing Sheets

ULTRASOUND SIGNAL PROCESSING ELECTRONICS WITH ACTIVE COOLING

FIELD THE INVENTION

This invention relates to ultrasonic transducers and, more particularly, to means for actively cooling electronics which are incorporated into a housing for an ultrasonic transducer.

BACKGROUND OF THE INVENTION

Transducers for use in medical ultrasound imaging applications generate heat during use. The FDA imposes limits on the maximum temperature that a patient contact surface may attain. The prior art has suggested various ways of cooling an ultrasonic transducer during operation. U.S. Pat. No. 5,560,362 to Sliwa Jr. et al. teaches various methods for providing active cooling to a transducer structure, per se, i.e., a closed loop circulating cooling system, a thermoelectric cooler and an evaporator/condenser system. In the embodiments described in the '362 patent, there is little consideration given to electronics which might be incorporated with the transducer.

U.S. Pat. No. 5,163,433 to Kagawa et al. and No. 4,748,985 to Nagasaki both disclose ultrasonic imaging heads with incorporated channels for the conduction of cooling liquid about an ultrasonic transducer structure.

As requirements placed upon the performance of ultrasound transducers have steadily increased, it has become important to capture the ultrasound signals as close to the transducer as possible. In this regard, electronic circuits have been incorporated directly into the housing which holds the transducer. So long as power dissipation from such circuits has been held to a minimum, the heat generated from such circuits has been able to be dissipated by straightforward conduction to an outer surface of the casing. However, as signal processing complexities required of such circuits has increased, the dissipated power has likewise increased. Accordingly, to preserve patient comfort and to enable transducer operation in a continuous manner, additional means must be found to provide necessary cooling of the included electronics. There is thus a need for improved means for cooling electronics incorporated into the housing of an ultrasound transducer. Further, there is a need to provide improved cooling means for integrated circuits incorporated into the ultrasound transducer housing.

SUMMARY OF THE INVENTION

An ultrasound transducer structure in accord with the invention includes: an ultrasound transducer operable to generate and receive ultrasonic energy, a communication cable, integrated circuits for processing signals received from said ultrasound transducer and flexible circuits for connecting the communication cable to the integrated circuit, and for further connecting the integrated circuits to the ultrasound transducer. A housing contains the ultrasound transducer, the integrated circuits and the flexible circuits. A heat transfer structure is positioned within the housing and is in contact with the integrated circuit. A heat conductor resides in contact with the heat transfer structure and conducts heat generated by the integrated circuits to a heat sink.

BRIEF DESCRIPTION OF THE DRAWINGS

FIG. 1b is a perspective view of the ultrasound transducer housing of FIG. 1a.

FIG. 2b is a perspective view of the ultrasound transducer housing of FIG. 2a.

FIG. 3b is a perspective view of the ultrasound transducer housing of FIG. 3a.

FIG. 4b is a perspective view of the ultrasound transducer housing of FIG. 4a.

FIG. 5b is a perspective view of the ultrasound transducer housing of FIG. 5a.

FIG. 6b is a perspective view of the ultrasound transducer housing of FIG. 5a.

FIG. 7b is a perspective view of the ultrasound transducer housing of FIG. 7a.

DETAILED DESCRIPTION OF THE PREFERRED EMBODIMENTS

Figure 1A:
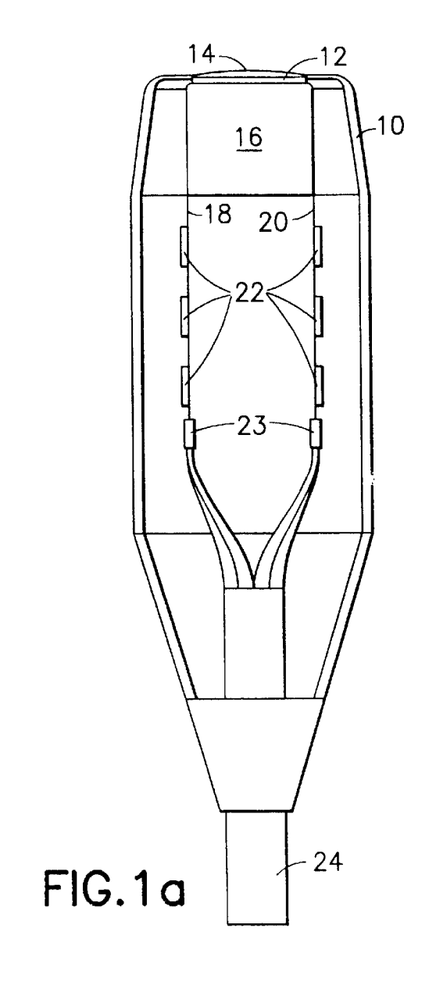
FIG. 1a is a plan view of an exemplary ultrasound transducer housing incorporating integrated circuits which require cooling.

Referring to FIG. 1, an ultrasound transducer housing 10 is illustrated, prior to inclusion of active cooling apparatus within its structure. Transducer housing 10 includes an acoustic crystal 12, an acoustic lens 14 and an acoustic backing 16. Connected to either side of acoustic crystal 12 are a pair of flexible circuit carriers 18 and 20, on which a plurality of integrated circuits 22 are mounted. Each of flexible circuit carriers 18 and 20 is electrically connected via a connector 23, to a cable 24 which exits transducer housing 10 at one extremity thereof.

Figure 1B:
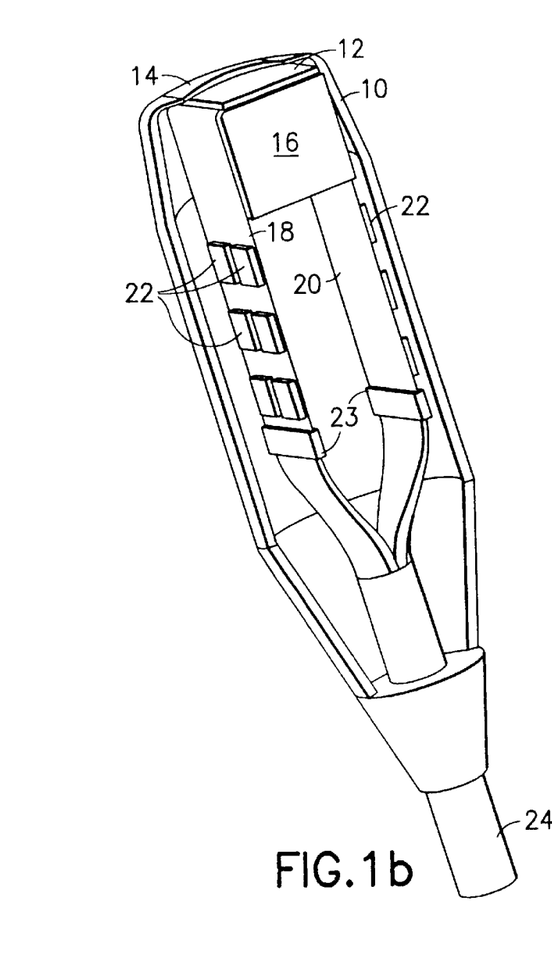

A perspective view of transducer housing 10, and its included components, is shown in FIG. 1b. It is to be noted that components which are commonly shown in each of the following FIGS. are numbered identically. A potting material (not shown) is incorporated within transducer housing 10 to provide structural support for circuit carriers 18, 20 and integrated circuits 22.

Due to the complex signal processing which is required to be performed on the signals emanating from acoustic crystal 12, a number of integrated circuits 22 are required to be positioned within transducer housing 10 and close to acoustic crystal 12. Such placement reduces the capacitance that is seen by the signals that are output from the transducer elements to the processing circuitry. Further, by positioning the processing circuitry within transducer housing 10, the transducer transmit voltages can be reduced due to the lessened capacitance that is seen. Also, because many ultrasound transducers comprise a large number of individual elements, close placement of the processing circuitry enables ready multiplexing of output signals therefrom and reduces the number of output conductors that are required.

Without proper levels of applied cooling, the heat generated by integrated circuits 22 will cause an unacceptable rise in the temperature of transducer housing 10. Accordingly, as shown in the following FIGS., the invention incorporates one or more active cooling features into transducer housing 10 to enable dissipation of internally generated heat.

Figure 2A:
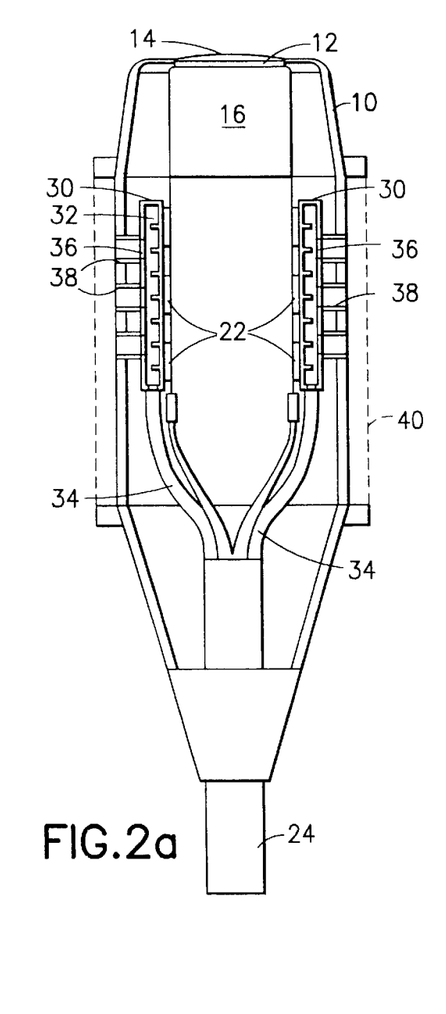
FIG. 2a is a plan view of an ultrasound transducer housing incorporating a gaseous cooling mechanism.
Figure 2B:
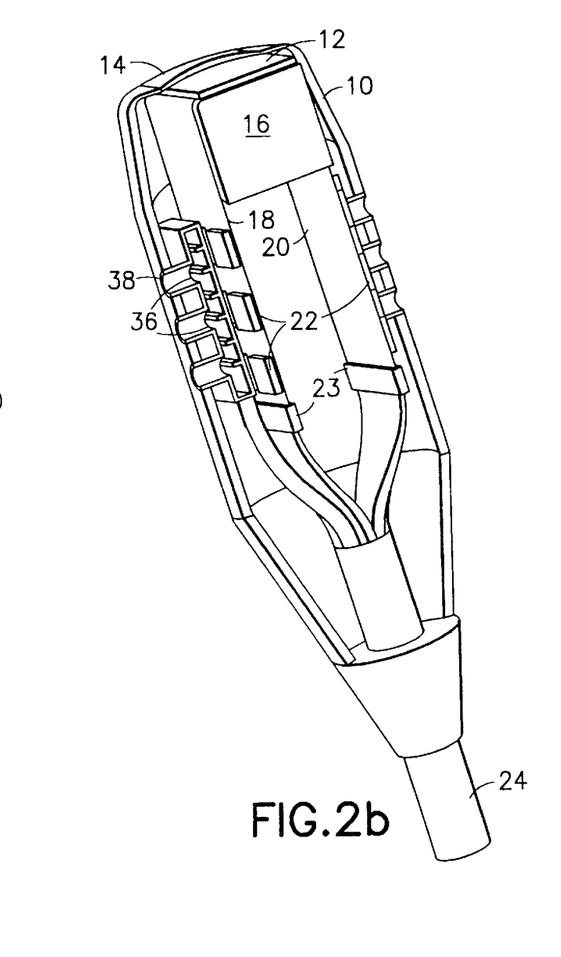

Referring to FIGS. 2a and 2b, to remove heat that is generated by integrated circuits 22, a high thermal conductivity heat exchanger 30 is mounted, either in direct contact with the upper surfaces of integrated circuits 22 or coupled thereto via a thermally transmissive grease. Heat exchanger 30 incorporates a hollow interior 32, wherein plural heat dissipating fins are positioned. A gaseous coolant tube 34 is coupled to one extremity of each of heat exchangers 30 and provides a flow of cooling air thereto. Gaseous coolant tubes 34 are preferably incorporated into cable 24 and either (i) receive a flow of cooling air from an externally positioned blower (not shown) or (ii) receive a flow of air that has been drawn into transducer housing through cooling openings integral thereto, by a remote suction action applied to coolant tubes 34.

A plurality of apertures 36 are formed in the upper surface of heat exchanger 30 and couple to a corresponding exit tube 38. Accordingly, cooling air introduced into heat exchanger 30 exits therefrom via apertures 36 and the associated exit tubes 38, along with heat generated by integrated circuits 22. A screen 40 (shown only in FIG. 2a) may be incorporated about transducer housing 10 to prevent a user's hand from blocking air flow through exit tubes 38.

Figure 3A:
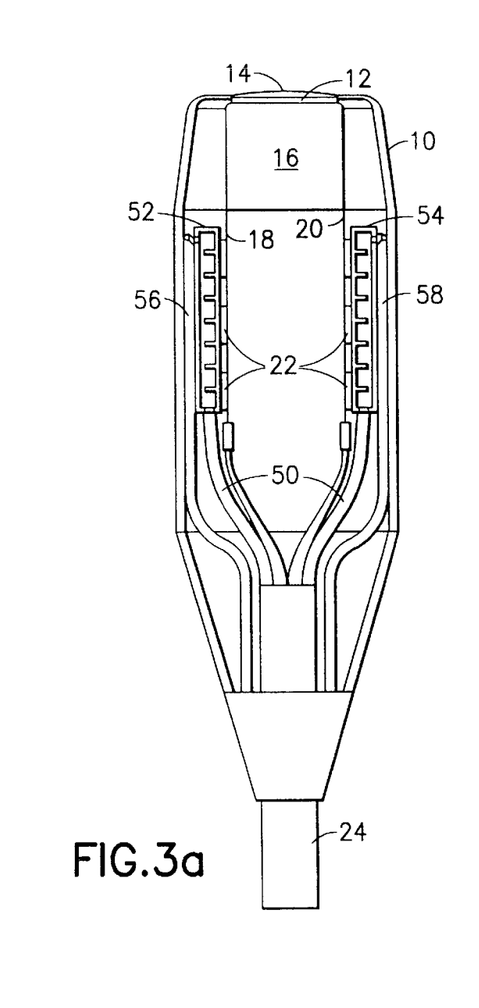
FIG. 3a is a plan view of an ultrasound transducer housing incorporating a liquid cooling mechanism.
Figure 3B:
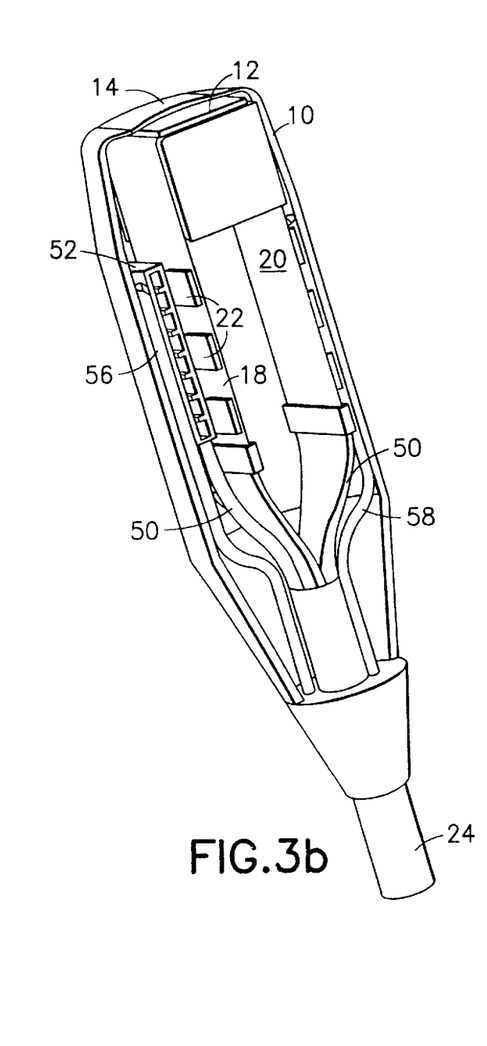

Referring to FIGS. 3a and 3b, a cooling arrangement in accordance with the invention is shown which incorporates both coolant feed and return paths within transducer housing 10. Coolant feed tubes 50 supply coolant to the interiors of heat exchange chambers 52 and 54. The coolant exits from heat exchange chambers 52 and 54 via coolant return tubes 56 and 58, respectively. Coolant return tubes 56 and 58 may be returned to a recirculating heat exchanger (not shown), wherein heat is removed from the coolant, prior to its being re-circulated. If the coolant fluid is air, it may be exhausted at the proximal end of transducer housing 10 or elsewhere.

Figure 4A:
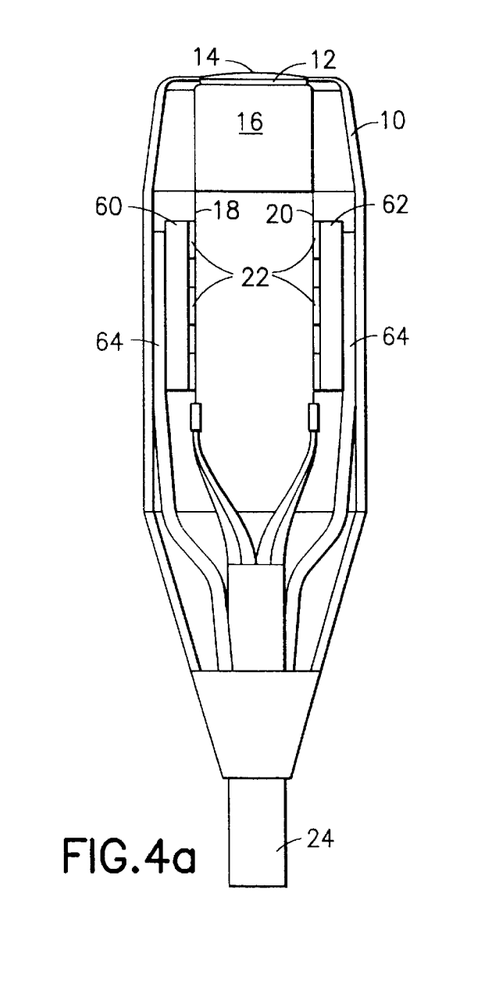
FIG. 4a is a plan view of an ultrasound transducer housing incorporating a solid heat conductor as the cooling mechanism.
Figure 4B:
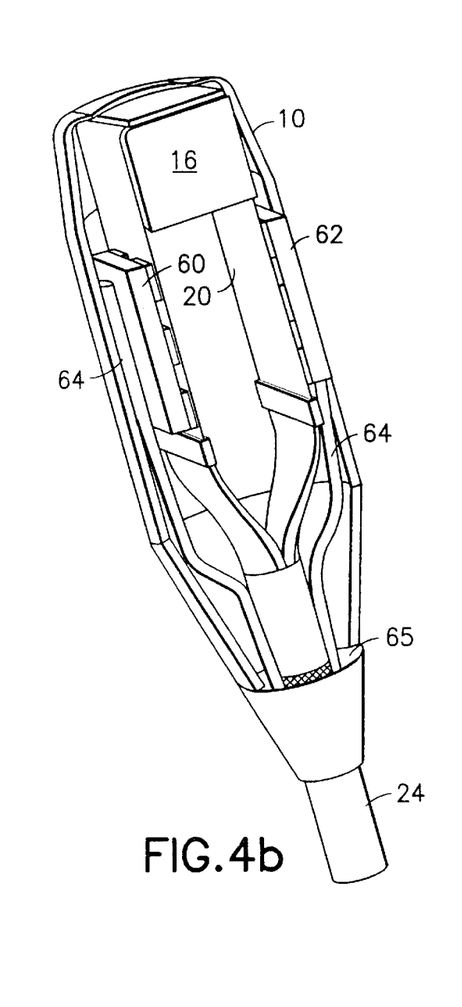

Referring to FIGS. 4a and 4b, a cooling arrangement is shown wherein solid heat conducting plates 60 and 62 are placed into contact with integrated circuits 22. A thermally conductive element 64 is coupled to each of heat conducting plates 60 and 62 so as to provide a heat removal path therefor. The proximal ends of thermally conductive elements 64 are preferably coupled to the ground shield conductor 65, which comprises a portion of cable 24. In such manner, shield conductor 65 (and the remainder of cable 24) act as a heat sink for thermally conductive elements 64.

Figure 5A:
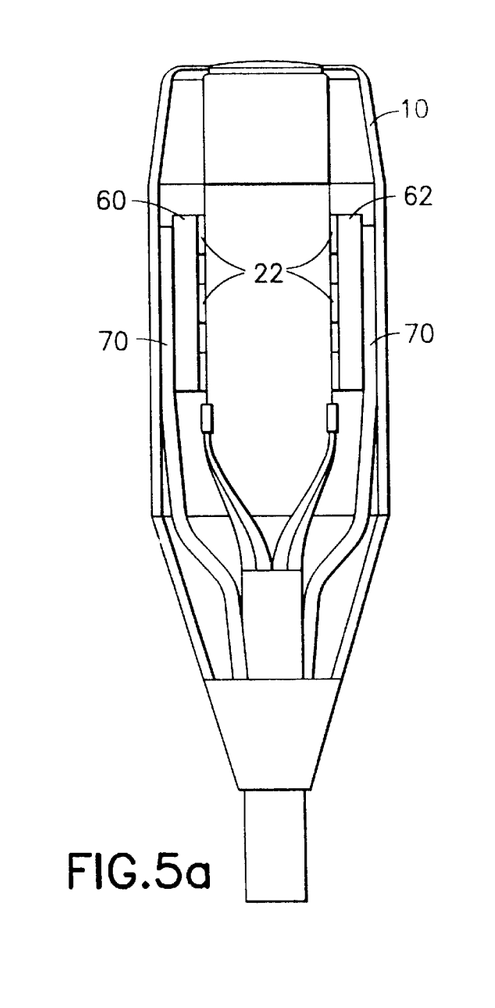
FIG. 5a shows a plan view of an ultrasound transducer housing incorporating a heat pipe as the cooling mechanism.
Figure 5B:
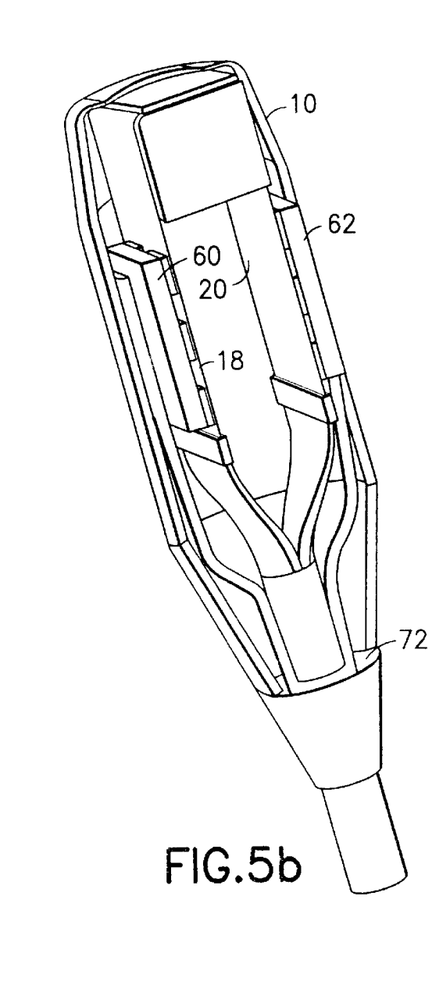

Referring to FIGS. 5a and 5b, a cooling arrangement is shown wherein thermally conductive elements 64 shown in FIGS. 4a and 4b are replaced by heat pipes 70. As known to those skilled in the art, a heat pipe comprises a sealed hollow tube having inner surfaces that incorporate a capillary wicking material. Inside the tube, a liquid, under its own pressure, enters the pores of the capillary material, wetting all internal surfaces. Applying heat to any point along the heat pipe surface causes liquid at that point to boil, and accordingly absorb heat. The resulting gas, which has a higher pressure, moves inside the sealed container to colder locations, where it condenses, giving up the latent heat of vaporization. Such action moves heat from the input region to be output end of the heat pipe.

As shown in FIG. 5b, the output ends of heat pipes 70 are coupled to a cable shield crimp and strain relief 72 to that is positioned at the proximal end of transducer housing 10.

Figure 6A:
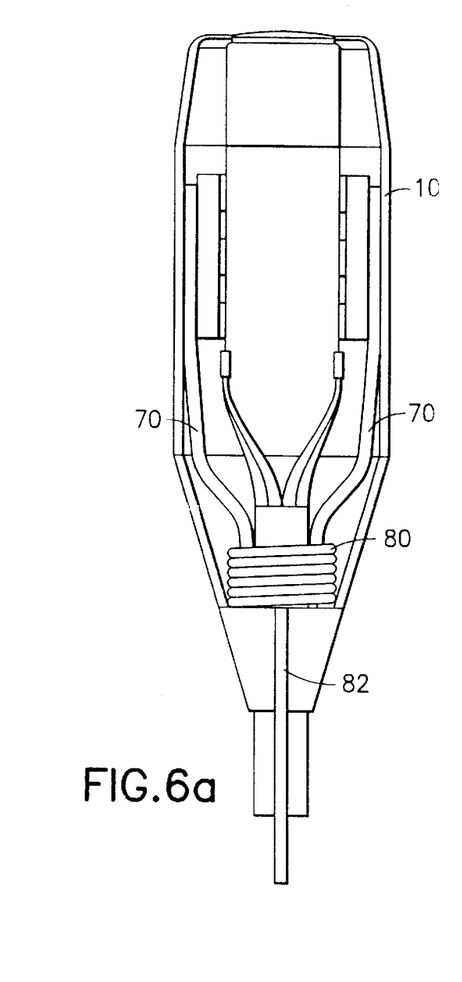
FIG. 6a is a plan view of an ultrasound transducer housing which incorporates an active heat exchanger into the transducer housing structure.
Figure 6B:
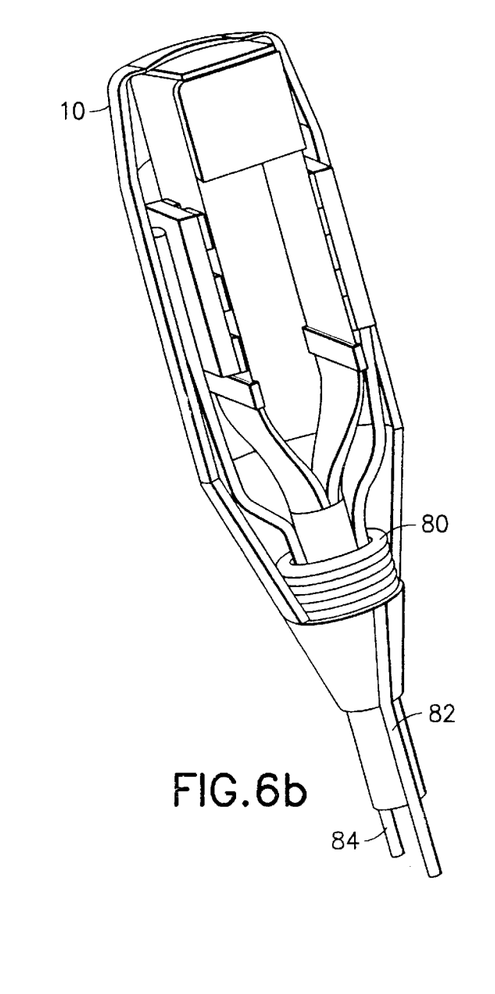

Instead of utilizing conduction to the cable heat sink to cool the output ends of heat pipes 70, an active heat exchanger may be incorporated into transducer housing 10. Such an arrangement shown in FIGS. 6a and 6b. There, a heat exchange coil 80 encircles the output ends of heat pipes 70. A coolant feed pipe 82 brings coolant to heat exchanger 80 and a return pipe 84 enables re-circulation of the heated coolant. Any liquid or gaseous coolant may be utilized with the embodiment shown in FIGS. 6a and 6b.

Figure 7A:
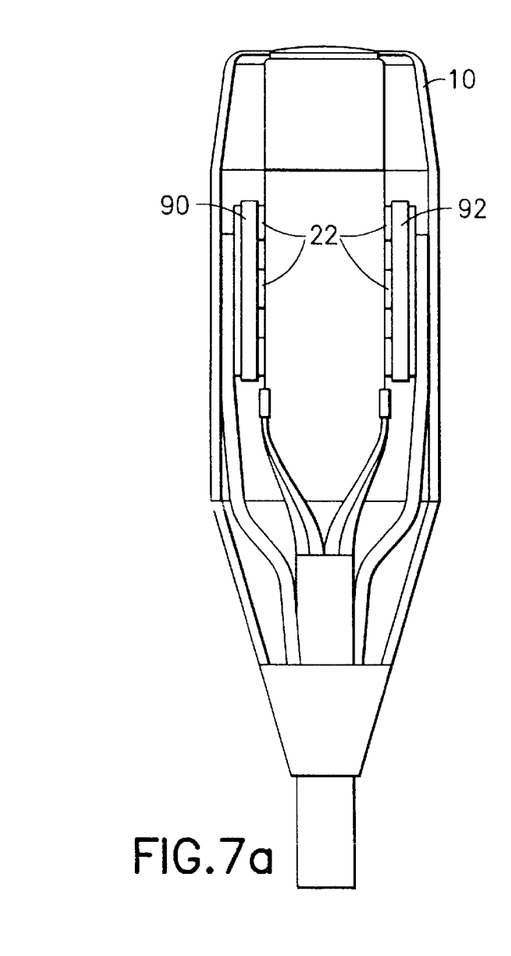
FIG. 7a is a plan view of an ultrasound transducer which incorporates a thermoelectric cooler into the transducer housing structure.
Figure 7B:
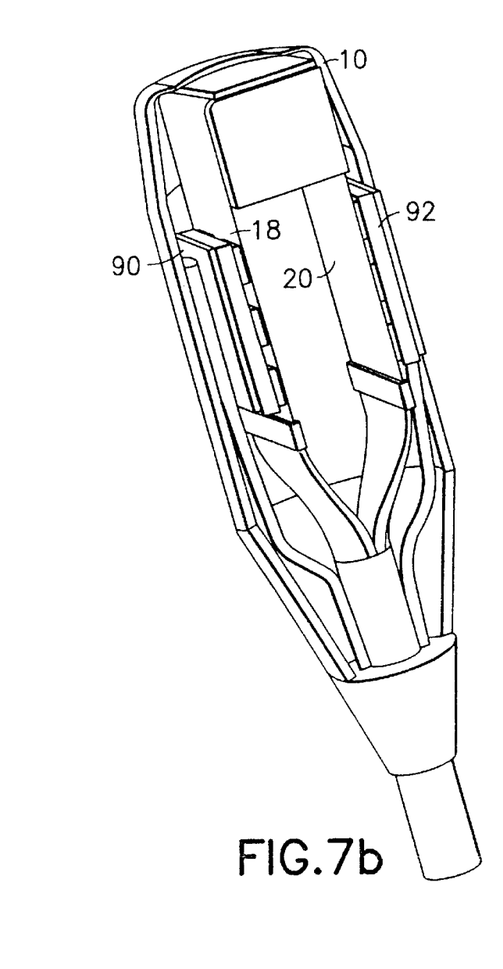

FIGS. 7a and 7b illustrate a further cooling embodiment which incorporates thermoelectric cooling modules adjacent integrated circuits 22. Such cooling modules have the ability to "pump" heat away from integrated circuits 22. By applying an electrical current to thermoelectric cooling modules 90 and 92, one surface of each module will cool and the other side will heat. Accordingly, thermoelectric cooling modules 90 and 92 are placed adjacent integrated circuits 22 to enable active cooling thereof. The heat generated at the outer surfaces of thermoelectric cooling modules 90 and 92 is removed by either direct conduction via a metallic heat conductor, by active cooling via a flow of cooling fluid, by action of a heat pipe or other direct heat removal technique.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

I claim:

1. An ultrasound transducer structure, comprising:

an ultrasound transducer operable to generate and receive ultrasonic energy;

a communication cable;

integrated circuit means for processing signals received from said ultrasound transducer;

circuit support means for connecting said communication cable to said integrated circuit means, and for further connecting said integrated circuit means to said ultrasound transducer;

a housing for containing said ultrasound transducer, said integrated circuit means and said circuit support means, said housing including heat transfer apertures;

a heat sink within said housing in contact with said integrated circuit means, and positioned in heat transfer relationship with said heat transfer apertures in said housing; and means for feeding a heat transfer fluid to said heat sink for conducting heat generated by said integrated circuit means and transferred to said heat sink to and through said heat transfer apertures.

2. An ultrasound transducer structure, comprising:

an ultrasound transducer operable to generate and receive ultrasonic energy;

a communication cable;

integrated circuits for processing signals received from said ultrasound transducer;

at least one flexible circuit substrate for connecting said communication cable to said integrated circuits, and for further connecting said integrated circuits to said ultrasound transducer;

a housing for containing said ultrasound transducer, said integrated circuits and said at least one circuit substrates;

a heat sink within said housing and in contact with each of said integrated circuits, said heat sink including an enclosed chamber; and fluid transfer means in contact with said heat sink, for feeding a heat transfer fluid to and through said enclosed chamber in said heat sink so as to conduct heat generated by said integrated circuits and transferred to said heat sink to a further heat transfer position.

3. The ultrasound transducer structure as recited in claim 2, wherein each said heat sink comprises a thermo-electric material.

4. The ultrasound transducer structure as recited in claim 2, wherein said heat transfer fluid is a liquid.

5. The ultrasound transducer structure as recited in claim 2, wherein said heat transfer fluid is air, said air being exhausted to the atmosphere.

6. An ultrasound transducer structure, comprising:

an ultrasound transducer operable to generate and receive ultrasonic energy;

a communication cable;

integrated circuits configured to process signals received from said ultrasound transducer;

at least one flexible circuit substrate connecting said communication cable to said integrated circuits, and further connecting said integrated circuits to said ultrasound transducer;

a housing containing said ultrasound transducer, said integrated circuits and said at least one circuit substrate;

a heat sink including an enclosed chamber within said housing and in contact with each of said integrated circuits; and fluid transfer ducts coupled to said enclosed chamber of said heat sink and configured to feed air to and through said enclosed chamber so as to conduct heat generated by said integrated circuits to a further heat transfer position.

7. The ultrasound transducer as recited in claim 6, wherein said further heat transfer position is an exhaust port to the atmosphere.

8. The ultrasound transducer structure as recited in claim 6, wherein each said heat sink comprises a thermo-electric material.

* * * * *